United States Patent [19]
Rook et al.

[11] Patent Number: 6,056,964
[45] Date of Patent: *May 2, 2000

[54] IMMUNOTHERAPEUTIC AGENT AND ITS USE

[75] Inventors: Graham Arthur William Rook; John Lawson Stanford, both of London, United Kingdom

[73] Assignee: Stanford Rook Limited, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/716,189

[22] PCT Filed: Mar. 29, 1995

[86] PCT No.: PCT/GB95/00715

§ 371 Date: Oct. 25, 1996

§ 102(e) Date: Oct. 25, 1996

[87] PCT Pub. No.: WO95/26742

PCT Pub. Date: Oct. 12, 1995

[51] Int. Cl.[7] .................................................. A61K 39/04
[52] U.S. Cl. ............................................................ 424/248.1
[58] Field of Search ........................................ 424/248.1

[56] References Cited

FOREIGN PATENT DOCUMENTS

WO 91/02542  3/1991  WIPO .
WO 93/16727  9/1993  WIPO .

OTHER PUBLICATIONS

International Journal of Immunopharmacology, vol. 7, No. 4, 1985 Aberdeen GB, pp. 515–524, Luisa MO (Moras et al).

*Primary Examiner*—Jerome D. Goldberg
*Attorney, Agent, or Firm*—Nixon & Vanderhye

[57] ABSTRACT

A method for delaying or preventing the growth or spread of a malignant neoplasm by administering to a subject in need material which comprises killed cells of *Mycobacterium vaccae* in an amount sufficient at least to delay or prevent the growth or spread of the neoplasm.

9 Claims, No Drawings

IMMUNOTHERAPEUTIC AGENT AND ITS USE

This application is a 371 of PCT/6B95/00715 filed Mar. 29, 1995.

This invention relates to immunotherapeutic agents useful in delaying or preventing the growth of tumours.

It has been suggested that the immune system is capable of preventing or delaying the growth of tumours at least in some cases, and some studies have tended to support this view. Thus Coley (W.B. 1894 "Treatment of Inoperable Malignant Tumours with toxins of erysipelas and the bacillus prodigiosus") described an immunotherapeutic method which appeared to be effective against a restricted range of tumours of mesodermal origin, by inducing a necrotizing mechanism similar to that induced by Koch's immunotherapy against tuberculosis. Since that time, most attempts at immunotherapy for cancer have aimed at inducing rapid tissue necrosis similar to that achieved in some cases by Coley.

It is known that there are at least 2 patterns of maturation of helper T cells, called TH1 and TH2. The former is associated with production of interleukin 2 (IL2), gamma interferon (IFN-γ), cytotoxic T cells (CTLs), reduced antibody production and down-regulation of production of TH2 cells. The latter produce IL4, IL5, enhance antibody production and down-regulate TH1 cells. The Koch phenomenon, probably induced by Coley's toxin, is thought to be the result of a mixture of TH1+TH2 matured cells.

It has been found that there are two categories of immune reactivity that can be harnessed for the control of tumours, and both can be evoked by Bacillus Calmette-Guerin vaccine (BCG). One is mechanism is tissue-destructive, as exemplified by Koch's and Coley's immunotherapies and by tumour immunotherapy with TNFα, and probably involves cytokine-mediated tissue damage in inflammatory sites appropriately prepared by the T cell-dependent Koch phenomenon. This mechanism appears to be effective against tumours of mesodermal origin. The second mechanism, based on immune recognition of the tumour cells themselves, might be effective against tumours of any origin. Indirect evidence for the existence of a non-specific TH1 based antitumour mechanism comes from the success of recombinant interleukin 12, a powerful TH1 inducer, in experimental cancers.

It is thought that Mycobacteria, if used in a way that avoids the induction of the Koch phenomenon, may be able to prime recognition of stressed autologous cells via heat shock protein (HSP) epitopes and epitopes of other proteins with highly conserved sequences, and so lead to selective tumour cell destruction. We conclude that the variable efficacy of BCG immunotherapy in the past was due to a failure to realise that BCG tends to boost the pattern of response already primed, as is emerging from studies of its efficacy in protection against tuberculosis and leprosy.

BCG as a vaccine against mycobacterial disease (both tuberculosis and leprosy) is very variable, giving anything from 80% protection to 0% protection in different studies. It is therefore significant that BCG given at birth appears in general to protect against childhood leukaemias only in those geographical locations where it protects against tuberculosis (Grange J M, Stanford J L. BCG vaccination and cancer. *Tubercle*. (1990); 71: 61–64). That is to say, it protects against both conditions in those places where it evokes a response to mycobacterial antigens that is not tissue-necrotising, and is not the Koch phenomenon.

Many tumour cells may present on their surfaces bacteriomimetic, carbohydrate, antigens and epitopes of stress proteins and other highly conserved proteins in relation to class 1 and class 2 major histocompatibility complex (MHC). Under circumstances of high antibody production, anti-carbohydrate antibodies originally raised against bacterial sugars, and perhaps IgA in type, could cover the tumour cells and block their surface components from cellular immune attack.

As we have shown in our International Application PCT/GB93/00463, immunotherapy with *M. vaccae* induces a predominantly TH1 pattern of response with macrophage activation by IFN-γ and little antibody production. Such TH1 responses are known to drive generation of CTLs. Marked reduction in production of antibodies, combined with increased numbers of CTLs would cause the tumour cells to become open to attack, both by macrophages activated after they had bound to the bacteriomimetic sugars on the tumour cell surface, and by the CTLs recognizing stress protein and other highly conserved protein epitopes presented by class 1 MHC. It is thought that the tissue necrotic mechanism via the Koch phenomenon is largely suppressed by the use of an *M. vaccae* derived preparation.

Immunotherapy with *M. vaccae* may therefore be expected to be effective against tumours of mesodermal, endodermal and ectodermal origin, including breast and bronchial tumours, by preventing or delaying the growth or spread of such tumours.

The present invention accordingly provides the use of antigenic and/or immunoregulatory materials derived from *Mycobacterium vaccae* for the manufacture of a medicament useful in delaying or preventing the growth and spread of tumours. Such material may be administered to a subject in an amount sufficient at least to delay or prevent the growth or spread of a tumour.

The therapeutic agent of the invention conveniently, and therefore preferably, comprises dead cells of *M. vaccae*, most preferably cells which have been killed by autoclaving. The immunotherapeutic agent normally comprises more than $10^8$ microorganisms per ml of diluent, and preferably from $10^8$ to $10^{11}$ killed *M. vaccae* microorganisms per ml of diluent. The invention includes within its scope antigenic and/or immunoregulatory material from *M. vaccae* for use in therapy to delay or prevent the growth or spread of a tumour.

The diluent may be pyrogen-free saline for injection alone, or a borate buffer of pH 8.0. The diluent should be sterile. A suitable borate buffer is:

| | |
|---|---|
| $Na_2B_4O_7.10H_2O$ | 3.63 g |
| $H_3BO_3$ | 5.25 g |
| NaCl | 6.19 g |
| Tween | 0.0005% |
| Distilled Water | to 1 liter |

The preferred strain of *M. vaccae* is one denoted R877R isolated from mud samples from the Lango district of Central Uganda (J. L. Stanford and R. C. Paul, Ann. Soc. Belge Med, Trop. 1973, 53, 141–389). The strain is a stable rough variant and can be identified as belonging to *M. vaccae* by biochemical and antigenic criteria (R. Bonicke, S. E. Juhasz., Zentr albl. Bakteriol. Parasitenkd. Infection skr. Hgy. Abt. 1, Orig., 1964, 192, 133).

The strain denoted R877R has been deposited at the National Collection of Type Cultures (NCTC) Central Public Health Laboratory, Colindale Avenue, London NW9 5HT, United Kingdom on Feb. 13th, 1984 under the number NCTC 11659.

For the preparation of the immunotherapeutic agent, the microorganism *M. vaccae* may be grown on a suitable solid medium. A modified Sauton's liquid medium is preferred (S. V. Boyden and E. Sorkin., J. Immunol, 1955, 75, 15) solidified with agar. Preferably the solid medium contains 1.3% agar.

The medium inoculated with the microorganisms is incubated aerobically to enable growth of the microorganisms to take place, generally at 32° C. for 10 days. The organisms are harvested, then weighed and suspended in a diluent. The diluent may be unbuffered saline but is preferably borate-buffered and contains a surfactant such as Tween 80 as described above. The suspension is diluted to give 100 mg of microorganism/ml. For further dilution, borate-buffered saline is preferably used so that the suspension contains 10 mg wet weight of microorganisms/ml of diluent. The suspension may then be dispensed into 5 ml multidose vials. Although the microorganisms in the vials may be killed using irradiation e.g. from $^{60}$Cobalt at a dose of 2.5 megarads, or by any other means, for example chemically, it is preferred to kill the microorganisms by autoclaving, for example at 10 psi for 10 minutes (115–125° C.). It has been discovered that autoclaving yields a more effective preparation than irradiation.

The immunotherapeutic agent is in general administered by injection to a volume in the range 0.1–0.2 ml, preferably 0.1 ml, given intradermally. A single dosage will generally contain from $10^7$ to $10^{10}$ killed *M. vaccae* microorganisms. It is preferred to administer to patients a single dose containing $10^8$ to $10^9$ killed *M. vaccae*. However, the dose may be repeated depending on the condition of the patient.

Although the immunotherapeutic agent will generally be administered by intradermal injection, other routes, e.g. oral administration, can also be used.

The invention includes within its scope a method for delaying or preventing the growth or spread of a tumour which comprises administering to a subject suffering from a tumour, antigenic and/or immunoregulatory material derived from *Mycobacterium vaccae* in an amount sufficient to provoke an immune response effective to delay or prevent the growth or spread of a tumour.

It may be advantageous and is within the scope of the invention to use more than one strain of *M. vaccae*, and/or to include in the therapeutic agent other mycobacterial antigens. Tuberculin may also be included.

The therapeutic agent may also contain BCG (Bacillus Calmette-Guerin) vaccine, in particular the freeze-dried form of the vaccine, to promote its effect.

The therapeutic agent can contain further ingredients such as adjuvants, preservatives, stabilisers etc. It may be supplied in sterile injectable liquid form or in sterile freeze-dried form which is reconstituted prior to use.

*M. vaccae* may be used as such or as an extract or fractionated portion of the organism to prepare therapeutic agents according to the invention.

The invention is further illustrated by the following Examples.

EXAMPLE 1

*M. vaccae* is grown on a solid medium comprising modified Sauton's medium solidified with 1.3% agar. The medium is inoculated with the microorganisms and incubated for 10 days at 32° C. to enable growth of the microorganism to take place. The microorganisms are then harvested and weighed and suspended in diluent to give 100 mg of microorganisms/ml of diluent. The suspension is then further diluted with buffered saline to give a suspension containing 10 mg wet weight of microorganism/ml of diluent and dispensed into 5 ml multidose vials. The vials containing the live microorganisms are then autoclaved for 10 minutes at 10 psi to kill the microorganisms and give the immunotherapeutic agent of the invention, which may (if desired) be further diluted for use.

This immunotherapeutic agent may be administered by intradermal injection in the manner already described.

EXAMPLE 2

Injections of *M. vaccae* have been administered to several tumour patients. Some of the results obtained are reported below:

Carcinoma of the Breast

1) At the National Institute of Hygiene and Epidemiology in Hanoi, Vietnam, where a number of studies are in progress using *Mycobacterium vaccae* as immunotherapy, a member of staff developed carcinoma of the breast with axillary secondaries. After operative removal she was advised to have BCG immunotherapy. Having seen such treatment regimes in others, the patient was not anxious to accept BCG, and requested treatment with *M. vaccae*. A standard injection of $10^9$ killed *M. vaccae* was given and for at least 3 years the patient has been well and without evidence of further tumour.

2) Within a few weeks of receiving an injection of *M. vaccae* for the treatment of persistant pityriasis, a woman aged 50 was found to have a breast lump on routine mammography. Biopsy showed the tumour to be malignant, and it was removed by lumpectomy. Histopathology showed marked sinus histiocytosis around axillary lymph nodes that were tumour-free. About 9 months later pityriasis returned and a second dose of *M. vaccae* was given, with almost immediate alleviation of the pityriasis. There were no signs of secondaries 21 months after removal of the tumour.

3) A woman in her early seventies had a tumour of the breast removed several years ago. She had a history of back pain due to arthritis for many years, and received an injection of *M. vaccae* in an attempt to relieve this. Very shortly afterwards X-ray of the spine showed a number of lesions considered to be secondary deposits of tumour, and she was referred for radiotherapy. After a delay of 8 weeks she presented for radiotherapy and on repeat radiography was found to have no signs of secondary deposits; radiotherapy was withheld. Two and a half years later she is well with no recurrence of tumours.

4) A general practitioner aged 55 presented with a 2-day history of what was thought to be an acute breast abscess. Incision showed the mass to be a very rapidly growing carcinoma, with secondary deposits already present in the axilla. Immediate removal was carried out, and injection of *M. vaccae* was given immediately after leaving hospital. Two further injections have followed at 3 month intervals. The operation wound healed well and after a year there is no evidence of secondary deposits in a patient in whom rapid progression of the disease was feared.

5) A nurse aged 50 who has complained of pain in the hip for a year was diagnosed as having bone secondaries from a small breast tumour. After an initial injection of *M. vaccae* she made good progress, withstood chemotherapy very well and had a second injection of *M. vaccae*. She is doing well.

Tumours of the Lung

1) A woman aged 55 developed breathlessness in October 1993 which was found to be due to several inoperable tumours in the lung. These were thought to be secondary deposits from an uncertain primary tumour. With the agreement of the oncologist, an injection of *M. vaccae* was given and a course of chemotherapy and radiotherapy was started. The patient withstood this with remarkably few side effects and did not want to have a second injection of *M. vaccae* when this was suggested after 6 months. Ten months after presentation her disease worsened, the chemotherapy was changed, but the patient was given a poor prognosis. A second injection of *M. vaccae* was given at the beginning of October 1994, following which the patients condition improved and she has had 2 further injections, one in December 1994, and a further injection on Mar. 1st 1995. Not only has this patient done much better than was expected, but she has borne 20 courses of chemotherapy without inconvenience.

Other Malignancies

1) A dentist of 30 years with terminal disease due to a malignant teratoma was given an injection of *M. vaccae* just before he was sent home to die. He showed signs of improvement within a day or two, and 3 weeks later showed reduction in size of visible tumours and was eating again for the first time in some weeks.

2) A woman of 36 developed adenocarcinoma of the stomach around an ulcer resulting from infection with *Helicobactorpylori*. She presented with numerous spreading secondaries despite chemotherapy. She has received a first injection of *M. vaccae* and it is intended to continue injections at 2-month intervals.

HIV-associated Tumours

1) A patient in the early phase of AIDS with multiple Kaposi's sarcomata received an injection of *M. vaccae* in November 1993. He has developed no further tumours, and his existing tumours show signs of resolution. A second injection of *M. vaccae* was given in December 1994 after he developed HIV-related secondary infections. He is to receive repeated injections of *M. vaccae* every 2 months.

2) A patient with almost no $CD4^+$ cells, but no overt signs of AIDS was given an injection of *M. vaccae* in June 1994, and a few weeks later was found to have a small KS lesion on one thigh about 0.5 cm in diameter. Further injections of *M. vaccae* were administered at 2-month intervals and in March 1995 the patient showed no further lesions and no increase in size of his initial lesion.

3) A man of 48 with multiple recurrent oropharyngeal carcinomata was given an injection of *M. vaccae* in June 1994 and further injections were given at 2-month intervals. By March 1995 there was no recurrence of the tumours.

The anecdotes set out above provide support for the treatment of tumours with *M. vaccae*. The use of *M. vaccae* has not been associated with any adverse side effects, indeed it may have helped in reducing toxic effects of chemotherapy in at least 2 of the patients. These early practical observations support the theoretical expectation and provide a first indication of valuable antitumour activity.

EXAMPLE 3

A preliminary experiment was carried out using Balb/c mice challenged with mouse mammary carcinoma strain MM3.

Three groups of 10 mice were challenged with $10^7$ MM3 cells. One week later a first group was injected with $10^7$ *M. vaccae*, a second group received $10^9$ *M. vaccae* and a third group acted as control. The animals were killed 40 days after challenge and examined for tumour development.

|  | Group 1 $10^7$ *M. vaccae* | Group 2 $10^9$ *M. vaccae* | Group 3 Controls |
| --- | --- | --- | --- |
| Tumours Developed | 1 | 2 | 5 |
| No tumours | 9 | 8 | 5 |

$p = 0.056$

What is claimed is:

1. A method for delaying or preventing the growth or spread of breast or bronchial neoplasm which comprises administering to a subject in need of same, antigenic and/or immunoregulatory material which comprises killed cells of *Mycobacterium vaccae* strain NCTC 11659 in an amount sufficient at least to delay or prevent the growth or spread of said neoplasm.

2. The method according to claim 1 herein the antigenic and/or immunoregulatory material is administered by intradermal injection.

3. A method for delaying or preventing the growth or spread of a malignant neoplasm sensitive to the material below which comprises administering to a subject in need of same, antigenic and/or immunoregulatory material which comprises killed cells of *Mycobacterium vaccae* strain NCTC 11659 in an amount sufficient at least to delay or prevent the growth or spread of said neoplasm.

4. The method according to claim 3 wherein the antigenic and/or immunoregulatory material is administered by intradermal injection.

5. The method according to claim 3 wherein the subject is administered a medicament comprising from $10^7$ to $10^{10}$ microorganisms per dose.

6. A method for delaying or preventing the growth or spread of a malignant neoplasm sensitive to the material below which comprises administering to a subject in need of same, antigenic and/or immunoregulatory material which comprises killed cells of *Mycobacterium vaccae* which produces the antireoplastic effect in an amount sufficient at least to delay or prevent the growth or spread of said neoplasm.

7. The method according to claim 1 wherein the neoplasm is a breast or bronchial neoplasm.

8. The method according to claim 1 wherein the subject is administered a medicament comprising from $10^7$ to $10^{10}$ microorganisms per dose.

9. The method according to claim 6 wherein the antigenic and/or immunoregulatory material is administered by intradermal injection.

* * * * *